US005626856A

United States Patent [19]
Berndt

[11] Patent Number: 5,626,856
[45] Date of Patent: *May 6, 1997

[54] COSMETIC DELIVERY VEHICLES AND RELATED COMPOSITIONS

[75] Inventor: Dieter Berndt, Incline Village, Nev.

[73] Assignee: Safe & Dry Company, Inc., Spring Lake, N.J.

[*] Notice: The term of this patent shall not extend beyond the expiration date of Pat. No. 5,338,535.

[21] Appl. No.: 497,454

[22] Filed: Jun. 30, 1995

[51] Int. Cl.$^6$ .................................................. A61K 9/48
[52] U.S. Cl. ........................... 424/401; 424/59; 424/65; 424/66; 424/68; 424/69; 514/844; 514/846
[58] Field of Search ............................ 424/401, 59, 65, 424/66, 68, 69; 514/844, 846

[56] References Cited

U.S. PATENT DOCUMENTS

| | | | |
|---|---|---|---|
| 4,780,145 | 10/1988 | Mori et al. | 106/206 |
| 4,857,307 | 8/1989 | Suss et al. | 424/63 |
| 4,913,896 | 4/1990 | Harvey | 424/69 |
| 4,921,701 | 5/1990 | Blehm Blank | 424/401 |
| 4,983,388 | 1/1991 | Kuwata | 424/401 |
| 5,013,763 | 5/1991 | Tubesing et al. | 514/772 |
| 5,069,897 | 12/1991 | Orr | 424/66 |
| 5,338,535 | 8/1994 | Berndt | 424/69 |

FOREIGN PATENT DOCUMENTS

| | | |
|---|---|---|
| 0310252 | 4/1989 | European Pat. Off. |
| 0317313 | 5/1989 | European Pat. Off. |

OTHER PUBLICATIONS

Patent Abstracts of Japan, vol. 11, No. 371 (C–462), 3 Dec. 1987.

Gennaro, "Remington's Pharmaceutical Sciences" pp. 774–775, 1318 (1985).

Disapio, "The Evolving Role of Silicones", Soap Cosmetics Chemical Specialties, Sep. 1994.

*Primary Examiner*—Jyothsna Venkat
*Attorney, Agent, or Firm*—Henry D. Coleman; R. Neil Sudol

[57] ABSTRACT

This invention discloses a novel delivery system for cosmetic, HBA and topical pharmaceutical products. The delivery system according to the present invention includes a volatile cyclosiloxane, a particulate carbohydrate and an oil or a glyceride ester. The carbohydrate and oil or glyceride ester are included in weight ratios which will produce a translucent film after the evaporation of the volatile cyclosiloxane from the composition. In addition, a number of other components may also be added to the delivery system including bioactive agents such as antiperspirant salts and antifungal agents, film-formers, surfactants, emollients, fragrances, coloring agents, preservatives, medicinals and related components depending upon the desired characteristics and the purpose for which the system and final product is designed.

42 Claims, No Drawings

COSMETIC DELIVERY VEHICLES AND RELATED COMPOSITIONS

FIELD OF THE INVENTION

The present invention relates to novel delivery vehicles for cosmetic and pharmacetucial compositons, including anti-perspirant compositions which exhibit superior tactile and other favorable physical characteristics.

BACKGROUND OF THE INVENTION

The health and beauty aids (HBA) industry has long depended on outdated delivery technology and cosmetic science. Many of the compounds and ingredients presently used have been in existence for hundreds of years. In particular, the formula for cold cream, developed in A.D. 200 by the Greek physician Galen, remained virtually unchanged throughout the early 1970's. In fact, it appeared that contemporary cosmetic science seemed to ignore new developments and discoveries in skin and hair biology. Although medical research was advancing at a rapid pace, particularly in the areas of aging, acne control and wound healing, until very recently, cosmetic manufacturers were reluctant to utilize the information derived from such research to produce novel cosmetic compositions.

No longer are HBA products simple concoctions of waxes and oils, extravagantly packaged and sold with even more extravagant marketing techniques. These products now contain active, effective ingredients developed through basic research and medical science and adapted for cosmetic chemistry. A host of new chemicals used in cosmetic products, such as the glycols and other alcohol derivatives, have become common additives in cosmetic products.

In the new cosmetics formulations, however, new additives sometimes become new skin irritants, merely replacing the old irritants. One of the primary reasons for adding these new additives is to produce a favorable effect in the product's characteristics, e.g. its feel, consistency, spreading effect, etc. These favorable characteristics, however, may be improved at the expense of skin irritation.

Little, if anything, has been done to develop a delivery vehicle for use in cosmetic products which can produce an end product which is truly hypoallergenic. By hypoallergenic, we mean that the product has a relatively small potential for invoking irritancy or an allergic reaction compared to current cosmetic or HBA products. The current wisdom is divided on what makes a product less irritating or hypoallergenic. According to a study conducted by the North American Contact Dermatitis Group (NACDG), fragrances were shown to cause approximately 50% of all known allergic reactions. In fact, numerous fragrances, especially including the complex esters are listed in the Hazardous Chemical Reference as being mild to strong irritants.

Removing the fragrances is one approach to solving the irritation problem. Even though all fragrances may be removed from a composition, the remaining ingredients may include allergenic and splotch-causing components. Very few of the manufacturers of hypoallergenic HBA or cosmetic products eliminate certain known skin irritants which the NACDG has found to be deleterious, for example, the preservatives, parabens and glycols. These substances are found in virtually every hair and skin care product on the market.

To complicate the problem of allergenic products, a number of other components which are quite often added to HBA products exhibit deleterious effects. For example, the inclusion of talcs, clays and phosphate-containing starches contribute to respiratory ailments in conjunction with dust mites. More seriously, talc has been implicated in a variety of human cancers, most notably, ovarian cancer. Dusting powders have been around for many years and may have escaped scrutiny as potentially harmful components. Recently, however, the American Pediatric Association has gone on record denouncing the use of dusting powders for use on infants because of the potential respiratory problems they can induce.

Nationwide opinion polls have reported that up to 50 percent of the population believes they have sensitive skin and have experienced adverse reactions to skin or hair care products.

Organosilicones are not found in nature and must be prepared synthetically. The ultimate starting material is sand (silicon dioxide) or other inorganic silicates, which make up 75% of the Earth's crust. The organosilicones were first synthesized in 1863 by Friedel and Crafts, who first prepared tetraethylsilane. In the following years, although many other derivatives were synthesized, it was not until the 1940's that widespread interest in organosilicon chemistry emerged.

Silicon is a relatively electropositive element that forms polar covalent bonds with carbon and other elements, including the halogens, nitrogen and oxygen. The strength and reactivity of silicon depend on the relative electronegativity of the element to which the silicone will be covalently bound. The polysilanes upon controlled hydrolysis readily form the polysiloxanes. These cyclic and linear polymers are commercially known as silicones. The cylic siloxanes are used in the present invention as delivery vehicles for body powders to provide compositions with unique characteristics.

The present invention has been developed to provide an alternative delivery system to traditional delivery systems, such system being both hypoallergenic and biologically compatible with the skin. It is also preferably ecologically friendly, i.e., substantially biodegradable or bioerodible.

In the case of anti-perspirant/deodorant formulations, under normal circumstances, it has been found very difficult to keep cyclomethicones within a stable solid or semi-solid suspension, especially when water and surfactants are not used. In prior art compositions, colloidal clays and fumed micro-ground silicone dioxide are used as thickeners and suspending agents for ingredients mixed with cyclomethicones. This approach has found some success in suspending fillers such as antiperpirant salts.

The prior art mixtures are primarily inorganic and have all the negatives of a topical skin irritant. Additionally, the products produce a noticeable white residue on the skin. The present invention addresses the problems found in these prior art compositions.

OBJECTS OF THE INVENTION

It is an object of the present invention to provide a novel delivery system for cosmetic, HBA and topically administered pharmaceutical products.

It is another object of the invention to provide a novel delivery system for cosmetic, HBA and topically administered pharmaceutical products sufficiently volatile to evaporate from the surface of the skin and leave behind the non-volatile components of the products.

It is still an additional object of the present invention to provide a delivery system which is hypoallergenic.

It is yet another object of the present invention to provide a novel delivery system which is substantially non-toxic and substantially biodegradable or bioerodible.

It is yet a further object of the present invention to provide a novel delivery system which can accommodate a wide range of components in cosmetic, HBA and topical pharmaceutical compositions.

It is still another object to provide a translucent delivery vehicle for cosmetic and pharmaceutical products which is cosmetically pleasing and which does not leave an opaque and/or white residue on the skin.

These and other objects of the present invention may be readily gleaned from the detailed description of the invention which follows.

BRIEF DESCRIPTION OF THE INVENTION

The present invention relates to the discovery that the inclusion of certain weight percentages of small particulate carbohydrates ("particulate carbohydrates") will enhance the volatility of cyclosiloxanes in formulations according to the present invention. In combination with an oil or glyceride ester, the starch will not only enhance evaporation of the cyclosiloxane from the surface of the skin, but will also leave a cosmetically pleasing translucent film on the surface of the skin after evaporation of cyclosiloxane. This discovery enables the manufacture and delivery of numerous cosmetic, HBA and topical pharmaceutical formulations which are hypoallergenic, safe, effective and which preferably exhibit an absence of toxicity and biocompatible, bioerodible and/or biodegradable characteristics.

The present invention relates to a novel delivery vehicle for cosmetic, HBA and topical pharmaceutical formulations consisting essentially of a volatile cyclosiloxane in combination with a particulate carbohydrate, the carbohydrate having the capability of enhancing the volatility of the cyclosiloxane compared to compositions containing the volatile siloxane alone. In addition to the volatile cyclosiloxane and particulate polymer, delivery vehicle compositions according to the present invention include at least one material selected from oils and glyceride esters, the combination of particulate carbohydrate and oils or glyceride esters producing a translucent film on the skin surface of a user of the material after the volatile cyclosiloxane material has evaporated. Compositions according to the present invention may also include various additional agents such as bioactive agents, including anti-perspirant salts, film-formers, surfactants, emollients, fragrances, coloring agents, preservatives, medicinals and related components depending upon the desired physical and chemical characteristics and the purpose for which the system and final product are designed.

There is a large variety and diversity of formulations which can be produced according to the instant invention not only in terms of the physical characteristics of the final products but also the vastly different chemical characteristics of the individual components which comprise the final product(s). The basic invention may be tailored for almost any type of Health and Beauty Aid product. Just the same, it is also effective as a topical pharmaceutical delivery vehicle/system allowing for the delivery of medication either for instant release or timed-release.

DETAILED DESCRIPTION OF THE INVENTION

As used herein, the following definitions will be used throughout the specification to describe the instant invention.

The terms "volatile cyclosiloxane", "cyclosiloxane", "volatile cyclomethicone" and "cyclomethicone" are used interchangeably to describe volatile siloxane compositions which find use in the instant invention. The volatile siloxanes which are included in the present invention are known to be somewhat volatile, although the volatility is generally limited at room temperature, with boiling points ranging from less than about 175° F. to over 200° F. The terms also include short chain volatile siloxanes (for example, linear polydimethylsiloxanes containing from 3 to 9 silicone atoms and having viscosities of less than about 10 cps).

Volatile cyclosiloxanes for use in the present invention include, for example, decamethylcyclopentasiloxane $[(CH_3)_2SiO]_5$ ("methyl pentamer"), octamethylcyclotetrasiloxane $[(CH_3)_2SiO]_4$ ("methyl tetramer"), dodecamethylcyclohexasiloxane $[(CH_3)_2SiO]_6$ ("methyl hexamer"), decaethylcyclopentasiloxane $[(CH_3CH_2)_2SiO]_5$ ("ethyl pentamer"), octaethylcyclotetrasiloxane $[(CH_3CH_2)_2SiO]_4$ ("ethyl tetramer") and dodecaethylcyclohexasiloxane $[(CH_3CH_2)_2SiO]_6$ ("ethyl hexamer"), and mixtures thereof. Preferred volatile cyclosiloxanes include decamethylcyclopentasiloxane, octamethylcyclotetrasiloxane and mixtures thereof. The term volatile cyclosiloxane also includes short chain siloxanes such as linear dimethylsiloxanes containing from 3 to 9 silicon atoms, preferably from 4 to 6 silicon atoms.

The term "particulate carbohydrate" is used throughout the specification to describe bio-compatible, preferably natural carbohydrate polymers which are compatible for use in pharmaceutical or cosmetic compositions, i.e., they are substantially non-toxic to biological systems, and they are biodegradable and/or bioerodible. These particulate carbohydrates have particle sizes which are generally less than about 100 microns in diameter, preferably less than about 20 microns in diameter. More preferably, they range in size from about 0.5 microns to about 10 microns. In general, particulate carbohydrate polymers having sizes which fall within the above range are added to the volatile cyclosiloxane in order to substantially enhance the volatility of the volatile cyclosiloxane compared to a system which excludes the carbohydrate polymer.

Exemplary natural particulate carbohydrate polymers include, for example, polysaccarides such as amylopectin, amylose, amylum (also commonly known as starch, which is comprised of a mixture of amylopectin and amylose), various specific starches such as rice starch, corn starch, potato starch, tapioca starch and wheat starch, among others, dextrin (a sugar amylum), glycogen (animal derived amylum), polysaccarides derived from algae including algin, carrageenan, agar, cellulose (from various plant sources) and cellulose ethers such as methyl cellulose, ethyl cellulose, hydroxyethyl cellulose, hydroxypropyl cellulose, carboxymethyl cellulose and related cellulose analogs, among others, including synthetic or crosslinked versions of the above-described carbohydrates. The various particulate carbohydrates may be used alone or in any combination in delivery vehicles according to the present invention.

The term "oil" is used throughout the specification to describe any of various greasy, combustible substances obtained from animal, vegetable and mineral matter. Oils for use in the present invention may include petroleum-based oil derivatives such as purified petrolatum and mineral oil which may be used in the present invention. Petroleum-derived oils include aliphatic or wax-based oils, including paraffin wax and oil, aromatic or asphalt-based oils and mixed base oils. In addition, certain essential oils derived from plants such as volatile liquids derived from flowers, stems and leaves and other parts of the plant which may include terpenoids and other natural products, may also be considered oils for purposes of the present invention. Beeswax paraffin may also be used in the present invention as an oil. Petrolatum (mineral fat, petroleum jelly or mineral jelly) and mineral oil products for use in the present invention are available commercially from a number of suppliers. These products may range widely in viscosity and other physical and chemical characteristics such as molecular weight and purity. Preferred petrolatum and mineral oil for use in the present invention are those which exhibit significant utility in cosmetic and pharmaceutical products. Pharmaceutical grade oils (USP) are preferred oils for use in the present invention.

The term "glyceride ester" is used throughout the specification to describe mono-, di- and tri- glycerides which may be added to the volatile cyclosiloxane and particulate carbohydrate in the present invention. These glyceride esters may be natural or synthetic (derived from esterification of glycerol and at least one organic acid, saturated or unsaturated, preferably a fatty acid, comprising between 8 and 22 carbon atoms) such as butyric, caproic, palmitic, stearic, oleic, linoleic or linolenic acids, among numerous others. Glyceride esters for use in the present invention include vegetable oils derived chiefly from seeds or nuts and including drying oils, for example, linseed, tung and oiticica; semi-drying oils, for example, soybean, sunflower, safflower and cottonseed oil; non-drying oils, for example castor and coconut oil; and inedible soap stocks, for example palm oil. Hydrogenated vegetable oils also may be used in the present invention. Animal oils are also contemplated for use as glyceride esters and include, for example, fats such as tallow, lard and stearin and liquid fats, such as fish oils, fish-liver oils and other animal oils, including sperm oil, among numerous others.

Preferred glyceride esters for use in the present invention include olein (a glyceride ester of oleic acid), linolein (a glyceride ester of linoleic acid), linolenin (a glyceride ester of linolenic acid), glyceride esters derived from at least two acids selected from oleic, linoleic and linolenic acid and triglycerides derived from one or more of oleic, linoleic and linolenic acid.

The term "translucent" is used throughout the specification to refer to the films containing the particulate carbohydrate and oil or glyceride ester which remain on the skin after the volatile cyclosiloxane evaporates from compositions according to the present invention. Translucent films are non-opaque, substantially colorless films which are partially transparent, permitting light to pass through diffusely (such that objects on the other side of the film cannot be distinguished). The transparent films according to the present invention, in some form, resemble frosted glass. For purposes of the present invention, translucent films are films which essentially hide or mask the white residue from the particulate carbohydrates which are included in compositions according to the present invention.

The present invention relates to novel cosmetic and pharmaceutical delivery compositions comprising a volatile cyclosiloxane and at least one particulate carbohydrate, in combination with an amount of an oil or ester of glyceride effective to render the particulate carbohydrate translucent after evaporation of the volatile cyclosiloxane from the composition. Other agents may be included in compositions according to the present invention such as bioactive agents, including anti-perspirant salts, film-formers, surfactants, emollients, fragrances, essential oils, coloring agents, preservatives, medicinals and related components depending upon the desired characteristics and the purpose for which the delivery system and final product are designed.

In the present invention, an effective amount of at least one volatile cyclosiloxane provides a favorable medium for the overall cosmetic delivery formulation. The cyclosiloxanes exhibit a unique cyclic or ring-like structure which make them very stable inert materials when combined with an effective amount of a particulate polymer and and an oil or glyceride ester. The cyclosiloxanes, and in particular, decamethyl-cyclopentasiloxane, have versatile chemical characteristics which may accommodate numerous additives to produce a large number of commercializable products in vastly different product categories. In a number of embodiments according to the present invention, a short chain linear polydimethylsiloxane (3 to 9 silicone atoms, more preferably 4 to 6 silicone atoms) may be substituted for the cyclosiloxane.

The volatility characteristics of the cyclosiloxanes make them particularly attractive substitutes for volatile alcohols such as methanol, ethanol and isopropanol in prior art cosmetic and pharmaceutical compositions. The inert chemical make-up of the cyclosiloxanes gives them a soft, smooth, soothing, no-stick, no-stain, no-sting, hypoallergenic character which is particularly useful in topical applications. Moreover, because of the inertness of the cyclosiloxanes, these may be used in numerous applications without affecting other components of the final compositions which may be somewhat chemically sensitive, e.g. to oxidation or hydrolysis.

A particularly preferred volatile cyclosiloxane for broad application in the instant invention is decamethylcyclopentasiloxane which has a low freezing point (−40°). Although this volatile cyclosiloxane is generally useful, the low freezing point of the methylpentamer makes it especially useful in products which are stored at low temperatures for long periods of time. Mixtures of decamethylcyclopentasiloxane and octamethylcyclotetrasiloxane are also useful for inclusion into compositions according to the present invention.

The present invention relates to cosmetic, HBA and topical pharmaceutical delivery systems in which a particulate carbohydrate, preferably a starch is added and mixed with such cyclomethicone silicone fluids as decamethylcyclopentasiloxane, octamethylcyclotetrasiloxane or other volatile cyclosiloxanes in combination with an oil or glyceride ester. In general, depending upon the intended use and the desired viscosity of the final composition (which may range from about 10 cps to thousands of cps), i.e., whether the final composition is to be in the form of an ointment, cream or lotion, the amount of volatile cyclosiloxane included in the delivery vehicle compositions according to the present invention ranges from less than about 10% to about 90% or more by weight, with a preferred range of about 10% to about 70% by weight, more preferably, as in the case of ointments and higher viscosity vehicles, about 15% to about 50% by weight, the remainder of the composition comprising a mixture of an oil or glyceride ester and a particulate carbohydrate. As a general rule, as the amount of volatile cyclosiloxane in the delivery vehicle increases, and the amount of particulate carbohydrate and/or oil or glyceride ester decreases, the viscosity of the delivery vehicle will decrease to form an ointment, a cream or a lotion. Obviously, the amount of volatile cyclosiloxane, particulate carbohydrate and oil or glyceride ester may be varied within the teachings of the present invention in order to change the physical characteristics, and in particular, the viscosity, of the delivery vehicle composition.

In addition to the volatile cyclomethicone, the delivery vehicle composition according to the present invention comprises an oil or glyceride ester in combination with a particulate carbohydrate, the weight ratio of the oil or glyceride ester to particulate carbohydrate ranges from about 5:1 to about 1:3, more preferably, about 5:1 to about 1:2, even more preferably, about 2:1 to about 1:2. In certain preferred compositions according to the present invention, for example, in the case of antiperspirant/deodorant compositions, the weight ratio of the oil or glyceride ester to particulate carbohydrate preferably ranges from about 1.5:1. Within the above-described weight ratio, the combination of the oil or glyceride ester and the particulate carbohydrate will produce a translucent film after the volatile cyclosiloxane evaporates from the surface of the skin, producing a cosmetically pleasing matrix which substantially eliminates or avoids the appearance of white residue from the particulate carbohydrate. While not being limited by way of theory, it is believed that an amount of oil or glyceride ester included within the range of weight ratios set forth above, scatters the light which would otherwise be absorbed by the particulate carbohydrate, producing a translucent film quality rather than an opaque or white residue.

The amount of particulate carbohydrate which is generally included in compositions which include volatile cyclosiloxane according to the present invention ranges from about 10% to about 65% or more by weight, preferably about 10% to about 50%. The amount of oil or glyceride ester generally ranges from about 5% to about 75% by weight, preferably about 10% to about 65% by weight. Of course, one of ordinary skill in the art will recognize that the inclusion of amounts of oil or glyceride ester and/or particulate carbohydrate outside of these ratios may also be effective, depending upon the characteristics of further additives which may be used and the ultimate characteristics of the final compositions desired. It is also noted that the particular component included in a composition according to a general product category, with reference to the desired final chemical characteristics of the composition (including, in particular, viscosity) may vary within a narrower range than the above-described weight ranges. The weight ratios of volatile cyclosiloxane, particulate carbohydrate and oil or glyceride ester will obviously be affected by the inclusion of other additives in the delivery vehicle compositions according to the present invention in order to provide a translucent quality of the film which appears on the skin after evaporation of the volatile cyclosiloxane.

In certain embodiments, the inclusion of one type of particulate carbohydrate or a volatility enhancer which acts like a particulate carbohydrate may reduce the need of the particulate carbohydrate to an amount which is less than the above-disclosed weight ratios. In other instances, it may be advisable to include the volatile cyclosiloxane in an amount which is substantially less than about 10% by weight of the composition, especially when other delivery vehicles or other components such as certain film-forming agents are included in the compositions. It is recognized that the above-described weight ratios should serve to guide, not limit, the formulation of compositions according to the present invention.

Below about 10% by weight of the delivery composition, the amount of cyclosiloxane may be too limited to provide the exceptional delivery characteristics that generally characterize the use of volatile cyclosiloxanes in this invention. When the amount of the particulate carbohydrate is significantly below about 10% by weight of the composition, this may reduce the volatility of the cyclosiloxane and the result may be a less desirable product. Above about 80% by weight particulate carbohydrate, and in many cases above about 65–70% by weight, the amount of starch may affect the translucency of the final film, i.e., making it significantly more opaque and less workable. In certain cases, the particles which constitute the carbohydrate may actually clump together into an undesirable consistency, a condition to be avoided, if possible.

One of ordinary skill in the art will understand to vary the weight ratio of cyclosiloxane, particulate carbohydrate and oil or glyceride ester within the teachings of the present invention to maximize the properties desired for a particular cosmetic or pharmaceutical effect, recognizing that the carbohydrate is included for its ability to enhance volatility and evaporation of the cyclosiloxane from the skin surface, and to instill favorable film characteristics of the final cosmetic or pharmaceutical composition after evaporation of the volatile cyclosiloxane. The volatile cyclosiloxane is included for its delivery characteristics, its volatility and its bio-erodibility and/or biodegradability and the oil or glyceride ester is included for its favorable film-forming characteristics and its ability to scatter light and produce a translucent quality in the final film on the skin.

The delivery compositions of the present invention may be used in numerous HBA and pharmaceutical products ranging from shampoos, anti-perspirants (soft-solid, stick, lotion or even aerosol), moisturizing lotions and creams, anti-acne creams and lotions, muscle and massage creams and lotions, sunscreens, insect repellents, anti-fungal preparations and numerous topical pharmaceutical preparations, among others.

Where an active agent is included in the delivery compositions, the amount of volatile cyclosiloxane ranges from about 10% to about 90% and the combination of oil or glyceride ester and particulate carbohydrate ranges from about 9.999% to about 89.999% by weight of the final composition, with the weight ratio of the oil or glyceride ester to particulate carbohydrate ranging from about 5:1 to about 1:3, more preferably, about 5:1 to about 1:2 and even more preferably about 2:1 to about 1:2. Within these weight ratios, a transluscent film can be formed after evaporation of the volatile cyclosiloxane. The active or other additives are included in final compositions according to the present invention in amounts ranging from about 0.001% to about 40% by weight of the final product composition. The term "final product composition" is used herein to describe the final HBA or pharmaceutical product which contains the delivery composition as well as the non-volatile components, including the active, which instill the composition with its cosmetic or pharmaceutical character.

The particulate carbohydrate is preferably included in the compositions according to the present invention in an amount effective to substantially accelerate or hasten the evaporation of the volatile cyclosiloxane by providing a spreading and dispersing medium for the volatile cyclosiloxane. The carbohydrates, and in particular, the polysaccharides are preferred because they are generally biologically compatible (non-toxic), biodegradable and/or bioerodible and inert, i.e., they will not produce any significant cross-reactivity, self-polymerization or other untoward effects on the other components which would be detrimental to or otherwise undesirable in the present compositions.

In certain product formulations, the polysaccharide group known as amylums or starches are particularly useful to instill variation in the compositions by providing a number of combinations of amylopectin (low temperature water-insoluble) and amylose (water-soluble) derivatives for effecting moisture absorbing or hygroscopic qualities to the compositions of the present invention.

The inclusion of polysaccharides in compositions according to the present invention provides the advantage that the polysaccharides can be doped or impregnated with a wide variety of soluble (preferably water soluble) active components which are added to serve a specific product function, e.g. an astringent for an anti-perspirant/deodorant. For example, amylum may be dissolved in water and mixed with an aluminum salt such as ALUM at a temperature of 38°–60° C. The mixture, which is subsequently dehydrated and reground into micro-fine particulates (generally, about 10 microns or less) becomes ALUM doped (impregnated) amylum.

Polysaccharides may also be added to the present invention to instill a natural moisture-absorbing character to the compositions. For example, amylum (a combination of amylose and amylopectin) exhibits a natural moisture (water) absorbancy. It is the amylose (low temperature water soluble) portion of the amylum which attracts or absorbs the moisture while it is in the amylopectin (low temperature water insoluble) polymer matrix. It is this feature of amylum which instills corn starch with its moisture absorbing characteristics. Corn starch, which has a moisture absorbing character, contains about 30% by weight amylose and about 70% by weight amylopectin.

Thus, compositions according to the present invention may be instilled with a basis for providing a more effective moisture absorbing composition. By increasing the amount of amylose in the particulate carbohydrate portion of the present invention, the moisture absorbing character of the composition may be dramatically increased, an unexpected result especially in compositions which contain high percentages of a volatile cyclosiloxane, which is considerably hydrophobic.

In addition to the volatile cyclosiloxane and particulate polymer, compositions according to the present invention include an effective amount of an oil or glyceride ester to instill translucent qualities to the film which remains after evaporation of the volatile cyclosiloxane. An oil or glyceride ester may be included in the present compositions in order to instill translucent qualities in a film containing the particulate carbohydrate, and to repel exogenous moisture and retain endogenous (natural skin) moisture. It has quite unexpectedly been discovered that the formulations according to the present invention which utilize oils such as mineral oil, paraffin or the petrolatum, among others or glyceride esters in combination with a particulate carbohydrate produces a micro-encapsulation of the carbohydrate. Upon evaporation of the cyclosiloxane, a film is formed which is produced by the microencapsulated particle linkage (oil or glyceride ester and particulate carbohydrate). The resulting film is both gas/air permeable and can be manufactured to repel or absorb moisture on the outside as well as hold onto or absorb moisture from the inside of the film. This film produced according to the present invention may be both bioerodible and biodegradable.

In the present compositions, an oil or glyceride ester is included. Preferred oils include mineral oil and petrolatum, among others. Preferred glyceride esters include mono-, di- and tri- glyceride esters derived from oleic, linoleic and linolenic acids and glycerol. These latter glyceride esters are used because of their characteristics of forming natural films on the surface of the skin and their biodegradability and bioerodibility.

When compositions according to the present invention are rubbed into the skin, the oil or glyceride ester and particulate carbohydrate are left behind in a translucent, preferably biodegradable matrix. The matrix is actually formed by the evaporation of the volatile silicone (cyclosiloxane) additive. Upon evaporation of the volatile silicone, tiny holes are left in the matrix formed by the oil or glyceride ester and the carbohydrate. These holes create a screen-like mesh which gives the matrix a gas permeability to the surrounding air. The mesh size of the film is small enough to allow the skin to breathe without obstruction, yet maintain the skin's moisture at its surface.

In most applications according to the present invention, a surfactant is not included. Consequently, films formed using these compositions does not easily wash off with water—thus giving these compositions a longer lasting natural inherent moisturizing quality. This feature provides the compositions according to the present invention with a dual-acting base as a moisturizer on the skin side (moisture is locked in) as well as a surface skin protectant (water soluble chemicals and hazardous liquids are locked out), in a gas permeable matrix.

The films which are produced from the compositions according to the present invention may also have sustained release characteristics. The film which is produced when compositions according to the present invention are rubbed onto the skin may be designed to change over time and with temperature changes (within a range of about 21° C. to about 49° C., more preferably about 23° C. to about 37° C.) such that the film when first applied will have a moisture-repellent/moisture retaining surface and later may acquire moisture absorbing characteristics as the volatile cyclosiloxane evaporates and the glyceride ester separates from the moisture-absorbing carbohydrate in the film. This effect can be particularly beneficial in many health and beauty aid products from anti-perspirants to liquid body powders because of the time/temperature release of certain active ingredients.

Depending upon the polysaccharide to glyceride ester weight ratio, a composition can be formulated to provide a film having a variety of product properties such as:

1. Moisture absorbancy on one side (skin side) of the membrane with moisture repellent properties on the outer side.

2. Instantaneous moisture absorbing properties.

3. Moisture absorbance/repellent characteristics which change over time and temperature.

The bio-matrix membrane may also provide the basis for the delivery of non-aqueous active ingredients such as essential oils which instill a fragrant scent and/or have medicinal value, for example eucalyptus (an inhalation expectorant), clove (a counterirritant/local anesthetic), citronella (as a perfume or insect repellent), witch hazel (as an astringent), as well as numerous other bioactive agents, especially including antiperspirant salts.

It is an unexpected result that the volatile cyclosiloxanes may be used as delivery vehicles for any number of cosmetic, HBA and pharmaceutical compositions. Although the cyclosiloxanes which are included in the present invention are known to be somewhat volatile, the volatility is generally limited at room temperature, with boiling points ranging from about 175° F. to over 200° F. Thus, although evaporation of a volatile cyclosiloxane from the skin would be expected to ultimately occur (usually, at least about 30 minutes after being delivered to a surface such as the skin), the volatility of the cyclosiloxanes, without the inclusion of effective amounts of a particulate polymer, preferably a particulate carbohydrate, is considered insufficient to be as useful as in the delivery compositions according to the present invention.

It has surprisingly been discovered that the volatile cyclosiloxanes will evaporate quickly from the surface of the skin when formulated with a particulate carbohydrate according to the present invention. Depending upon the amount of particulate carbohydrate included in the compositions, this may actually enhance the evaporation of the cyclosiloxane. While not being limited by way of theory, it is believed that this unexpected result may occur because the inclusion of the carbohydrate serves to disperse the cyclosiloxane delivery vehicle, thus maximizing surface area to which the cyclosiloxanes are exposed. It is believed that the dispersion action of the particulate polymer within the cyclomethicone delivery vehicle significantly increases the evaporation of the formulated cyclosiloxane relative to non-dispersed cyclosiloxane. The result is an unexpectedly enhanced evaporation of the cyclosiloxane delivery vehicle from the surface of the skin. In essence, the cyclomethicone and particulate carbohydrate work hand-in-hand to produce a system wherein the cyclosiloxane evaporates significantly faster when formulated with the polymer than without the polymer. It is noted that the tendency of the particulate carbohydrate to enhance the evaporation of the volatile cyclosiloxane is a feature which may be used to formulate compositions according to the present invention.

In addition to the volatile cyclosiloxane, particulate carbohydrate and an oil (including mineral oils and petrolatum) or a glyceride ester, compositions according to the present invention may also include both inert and active agents, for example, fragrances and coloring additives, emollients such as lanolin, propylene glycol and glycerine, among others, surfactants such as polysorbate 20, 60, 80 and 85, Miranate SSB, various Tween surfactants such as Tween 60 and 80, and Neodol 25-3S, among numerous other surfactants well known in the art, film formers such as dimethicone (which may also function as an emolient), polyvinylpyrrolidone and other film-forming polymers and medicinals such as camphor, menthol, capsaicin, zinc oxide and sulfur, among numerous others, including vitamins such as vitamin A, D and E, as well as anti-perspirant salts, in amounts ranging from about 0.001% to about 40% by weight of the final composition.

In the case of fragrances and coloring agents, these additives are generally included in effective amounts, i.e., generally no more than about 1% by weight of the final composition. In the case of surfactants and emollients, these components are added in amounts generally effective to produce the intended effect and generally about 0.01% to about 20% by weight of the final composition. In addition, the inclusion of bioactive agents, such as anti-fungal agents and assorted antimicrobial agents is a further aspect according to the present invention.

Antiperspirant/deodorant compositions are also contemplated by the present invention. Antiperspirant materials may be included in compositions according to the present invention, generally in amounts ranging from about 5% to about 35% by weight, preferably about 15% to about 35% by weight, more preferably about 20% to about 30% by weight. Antiperspirant materials may include any compound or composition having antiperspirant activity and such materials include various antiperspirant salts, such as astringent metallic salts, including inorganic and organic salts of aluminum, zirconium and zinc and mixtures thereof. Other antiperspirant salts which may be used in the antiperspirant compositions according to the present invention include aluminum halides, aluminum hydroxy halides, zirconyloxide halides, aluminum chlorhydroxide salts, zirconyl hydroxychlorides, among numerous others, including zirconium salt complexes which also contain aluminum and glycine, known as "ZAG" complexes. In addition, other natural product antiperspirant materials such as oil of witch hazel as well as tea tree oil may be used in the instant invention. Antiperspirant materials for inclusion in compositions according to the present invention are well known in the art.

Although the weight ratios of the volatile cyclosiloxane and the mixture of particulate carbohydrate and oil or glyceride ester will fall within the general weight ratios outlined in this specification, two preferred embodiments of antiperspirant compositions are contemplated by the present invention.

In a liquid or roll-on antiperspirant composition, the amount of volatile cyclosiloxane generally ranges from about 35-70% by weight, the mixture of particulate carbohydrate and oil or glyceride ester about 15% to about 40% by weight and the amount of the antiperspirant material preferably ranges from about 15% to about 35%, more preferably about 20% to about 30% by weight. In antiperspirant compositions which are characterized in the art as being "soft-solid" compositions, these compositions comprise about 15% to about 50% by weight volatile cyclosiloxane, about 20% to about 55% by weight of a mixture of particulate carbohydrate and an oil or glyceride ester and about 15% to about 35% by weight, more preferably about 20% to about 30% by weight. In antiperspirant compositions according to the present invention, in order to maintain a translucent film, the weight ratio of the oil or glyceride ester to particulate carbohydrate in the antiperspirant compositions according to the present invention ranges from about 5:1 to about 1:3, preferably about 5:1 to about 1:2, more preferably about 2:1 to about 1:1, even more preferably about 1.5:1 to about 1:1. It is noted that the inclusion of milled particulate carbohydrates having particle sizes of about 10 microns or less produces a composition having a smooth feel to it—in contrast to prior art compositions which generally include organoclay thickeners, for example, the "bentonites", which produce a "gritty" feel.

One of ordinary skill in the art without undue experimentation will recognize to include a particular agent in compositions according to the present invention for the agent's known benefit in amounts which would produce an intended result without substantially impacting the overall favorable characteristics of compositions according to the present invention.

In another embodiment according to the present invention, the volatile cyclosiloxane may be entirely eliminated from the composition. In this aspect of the present invention, the inclusion of a particulate carbohydrate powder, most preferably a starch, in combination with an oil or glyceride ester, preferably petroleum jelly, at a weight ratio of oil or glyceride ester to particulate carbohydrate of about 5:1 to about 1:3, more preferably about 5:1 to about 1:2, even more preferably about 2:1 to about 1:2, produces a fast drying, non-greasy translucent film when applied to the skin. In this aspect of the present invention, the particulate carbohydrate, most preferably, starch, ranges from about 10% to about 70% by weight of the composition and the oil or glyceride ester ranges from about 20% to about 85% by weight of the composition, with further optional additives such as active agents selected from the group consisting of antifungal agents, antiperspirant materials, antimicrobial agents, anti-inflammatory agents, anti-puritic agents, anti-acne agents, hemostatic agents, anti-histaminic agents, medicinals and mixtures, thereof, and other additives including fragrances, coloring additives, emollients, surfactants and film formers ranging in weight from about 0.001% to about 40% by weight of the composition.

The following bioactive agents, among a large assortment of others, may be included in the compositions according to the present invention to produce a wide variety of pharmacologically active formulations:

Anti-Fungals
   Terconazole
   Econozole
   Hamycin
   Mepartricin

Antibiotics/Anti-Bacterials
   Nifutoinol
   Miloxacin
   Sulfadiazine
   Thiazolsulfone
   Cefadroxil Anti-Inflammatory
   Fenoprofen
   Acemeticin
   Acetylsalicylic acid
   Salicetamide Anti-Puritic
   Camphor
   Menthol
   Risocaine
   Phenol
   Dichlorisone Anti-Acne
   Benzoyl Peroxide
   Dichloroacetic Acid
   Salicylic Acid
   Tetroquinone Hemostatic
   Algin
   Alginic Acid
   Ellagic Acid
   Vasopressin
   Thrombin
   Cephalin Anti-Histaminic
   Dimethindene
   Bamipine
   Triprolidine
   Setastine
   Promethazine These agents are generally included in compositions according to the present invention in amounts ranging from about 0.001% to about 40% or more by weight, depending upon the activity of the agent included and the intended use of the composition.

The final cosmetic or pharmaceutical compositions using the present delivery vehicle compositions may be applied to the body as a cream, liquid or solid (ointment or semi-solid). After being rubbed in place, evaporation of the cyclosiloxane proceeds, leaving the non-volatile components behind in a translucent film. The compositions thus may be formulated to deposit any number of agents in the cracks and crevices of the skin, without leaving any irritants, toxic particles or liquid residues which occur in the prior art compositions.

Another aspect according to the present invention relates to a preferred method of making the novel delivery compositions. It generally has been found preferable to mix and mill the cyclosiloxane in the presence of the particulate polymer first and then add the oil or glyceride ester in order to benefit from the interaction of the cyclosiloxane, particulate polymer and other additives. Preferably, the mixing occurs by combining the individual components under shearing force in a homogenizer/mixer. In preferred embodiments, the homogenization process produces submicron particles within a volatile silicone fluid, thus creating an open-core micro-encapsulated material with a wide range of viscosities (i.e., lotion, cream, ointment or semi-solid).

In certain aspects of the present invention, it is preferable to mix the particulate carbohydrate and volatile cyclosiloxane at a ratio of about 50/50 solids to liquid ratio. This initial mix can be performed at room temperature (65°–85° F.), utilizing any conventional laboratory or production mixing apparatus. The resulting mixture will have a viscosity range between about 40 and 70 cps. To this mixture, the oil or glyceride ester is added, typically at a temperature of about 175° F., in amounts generally ranging from about 10% to about 50% or more by weight of the mixture (depending upon the weight percentage of the oil or glyceride ester in the final delivery composition). These components are mixed together at higher speeds, and the temperature of the total mixture is brought to about 150° F. A homo-mixer (any type or model), with shearing blades which are adjustable from about 1 to 10 microns, is connected to a circulating pump which pumps the mixture out of the mixing vat to the homomixer. The sheared mixture then empties into a second heated vat where another pump circulates the mixture through the homomixer. When all of the mixture is emptied out of the initial mixing vat, that pump is shut-off and the mixture is allowed to shear and circulate in the second vat for about an hour or until a uniform micro-particle structure is achieved. Once the delivery vehicle composition is made, the final product composition may be made by adding further components such as the active agents which are added to instill the final product composition with the desired cosmetic or pharmaceutical character.

Alternatively, the ingredients (which may include the active or additional components other than volatile cyclosiloxane, particulate carbohydrate and oil or glyceride ester) may be added directly to a heated pebble mixer or ball mill which has the ability to microsize the particles in the composition (less than about 10 microns in diameter). The resulting product will be virtually the same as that cited for the homomixer.

The following examples are provided to illustrate the present invention and should not be construed to limit the scope of the invention in any way. In making the compositions set forth below, the above-described methodology utilizing the homomixer is preferably used, where applicable.

| Component | % By Weight |
|---|---|
| Example 1 Antiperspirant Formulations | |
| Formula A | |
| Cyclonethicone (Tetramer GE SF-1173) | 45 |
| Starch (National Starch Dry Flo) | 10 |
| White Petrolatum (USP Grade) | 15 |
| Isopropyl Palmitate (Henkel) | 5 |
| Zirconium-Aluminum Chlorhydrex (GLY) | 25 |
| Fragrance | |

Formula B

| | |
|---|---|
| Cyclomethicone (Tetramer GE SF-1173) | 20 |
| Cyclomethicone (Pentamer GE SF-1173) | 25 |
| Starch (National Starch Dry Flo) | 15 |
| White Petrolatum (USP Grade) | 12 |
| Mineral Oil (USP) | 5 |
| ZAG (Salts) | 23 |
| Fragrance | |

Formula C

| | |
|---|---|
| Cyclomethicone (Tetramer GE SF-1173) | 50 |
| Starch (National Starch Dry Flo) | 15 |
| White Petrolatum (USP Grade) | 15 |
| ZAG (Salts) | 23 |
| Fragrance | |

Formula D

| | |
|---|---|
| Cyclomethicone (Tetramer GE SF-1173) | 30 |
| Cyclomethicone (Pentamer GE SF-1173) | 15 |
| Starch (National Starch Dry Flo) | 10 |
| Polydimethylsiloxane Gum (GE SF-1214) | 10 |
| White Petrolatum (USP Grade) | 15 |
| ZAG (Salts) | 25 |
| Fragrance | |

| Component | Optimum Wt % | Formula Range |
|---|---|---|

Example 2
Liquid Roll-On Antiperspirant/Deodorant

| | | |
|---|---|---|
| Cyclomethicone (Tetramer or Pentamer) | 50 | 35–70 |
| Starch (National Starch Dry Flo) | 10 | 5–20 |
| White Petrolatum (USP Grade) | 15 | 5–20 |
| Zirconium Aluminum Tetra-Chlorhydrex GLY | 25 | 20–30 |

Example 3
Soft-Solid Antiperspirant/Deodorant

| | | |
|---|---|---|
| Cyclomethicone (Tetramer or Pentamer) | 40 | 15–50 |
| Starch (National Starch Dry Flo) | 25 | 15–35 |
| White Petrolatum (USP Grade) | 5 | 2.5–10 |
| Paraffin (USP) | 5 | 2.5–10 |
| Zirconium Aluminum Tetra-Chlorhydrex GLY | 25 | 20–30 |

Example 4
Dry Petrolatum

| | | |
|---|---|---|
| White Petrolatum (USP Grade) | 43 | 23–63 |
| Cyclomethicone (Tetramer or Pentamer) | 17 | 10–30 |
| Starch (Dry Flo or Crosslinked) | 40 | 15–50 |

Example 5
Translucent Body Powder

| | | |
|---|---|---|
| White Petrolatum (USP Grade) | 10 | 5–15 |
| Mineral Oil (USP Grade) | 15 | 10–20 |
| Cyclomethicone (Tetramer or Pentamer) | 25 | 13–40 |
| Starch (National Starch Purity 21C) | 50 | 30–60 |

Example 6
Dry Moisturizing Cream

| | | |
|---|---|---|
| White Petrolatum (USP Grade) | 40 | 20–40 |
| Mineral Oil (USP Grade) | 10 | 5–15 |
| Cyclomethicone (Tetramer or Pentamer) | 20 | 10–30 |
| Starch (National Starch Purity 21C) | 30 | 20–40 |

Example 7
Acne/Facial Blemish Cream

| | | |
|---|---|---|
| White Petrolatum (USP Grade) | 43 | 20–40 |
| Mineral Oil (USP Grade) | 10 | 5–20 |
| Cyclomethicone (Tetramer or Pentamer) | 10 | 5–20 |
| Starch (Dry Flo) | 27 | 20–40 |
| Benzoyl Peroxide (Active) | 10 | 5–15 |

Example 8
Waterproof Sunblocker

| | | |
|---|---|---|
| White Petrolatum (USP Grade) | 40 | 20–60 |
| Mineral Oil (USP Grade) | 5 | 1–10 |
| Cyclomethicone (Tetramer or Pentamer) | 15 | 10–20 |
| Starch (Dry Flo) | 32 | 20–40 |
| Benzophenone-3 | 2 | 1–10 |
| Octocrylene | 3 | 1–10 |
| Octyl Methoxycinnamate | 3 | 1–10 |

Example 9
Vitamin E Skin Cream/Moisturizer

| | | |
|---|---|---|
| White Petrolatum (USP Grade) | 40 | 20–60 |
| Mineral Oil (USP Grade) | 10 | 5–15 |
| Cyclonethicone (Tetramer or Pentamer) | 20 | 10–20 |
| Starch (Purity 21C) | 27 | 15–40 |
| Tocopheryl Acetate | 3 | 1–10 |

Example 10
Topical Analgesic Rub (For Arthritis Pain)

| | | |
|---|---|---|
| White Petrolatum (USP Grade) | 40 | 20–40 |
| Mineral Oil (USP Grade) | 10 | 5–15 |
| Cyclomethicone (Tetramer or Pentamer) | 15 | 10–20 |
| Starch (Purity 21C) | 35 | 30–40 |
| Camphor | 4 | 2–10 |
| Capsaicin | 0.025 | 0.020–0.030 |

| Component | Optimum Weight % Range |
|---|---|

Example 11
Film Formers Without Volatile Cyclosiloxane

Sample 1

| | |
|---|---|
| Cornstarch (modified or unmodified) | 10–70 |
| Petrolatum | 20–85 |

Sample 2

| | |
|---|---|
| Cornstarch (modified or unmodified) | 10–70 |
| Mineral Oil | 20–85 |

Sample 3

| | |
|---|---|
| Cornstarch (modified or unmodified) | 10–70 |
| Isopropyl Palmitate | 20–85 |

Sample 3

| | |
|---|---|
| Cornstarch (modified or unmodified) | 10–70 |
| Petrolatum | 10–45 |
| Mineral Oil | 10–45 |

While there has been described what is considered to be preferred embodiments of the present invention, it will be readily apparent to those skilled in the art that modifications to the present invention can be made without departing from the scope of the teachings herein. As will be appreciated, the volatile cyclosiloxane evaporates over time into pure silicone dioxide and carbon dioxide gases, which are completely non-toxic, completely inert, and provide substantially no negative byproducts. Although the inclusion of amylum and other polysaccharide powders in many instances produces a preferable product, other relative percentages and other particulate polymers, whether synthetic or nature, may be employed, to essentially control the viscosity, rate of evaporation of the silicone fluid, and the amount of polymer left behind. All of such choices are well within the skill of the routineer—and, for such reasons, resort should be had to the claims appended hereto for a true understanding of the scope of the invention.

I claim:

1. A delivery composition for use in a cosmetic or pharmaceutical formulation consisting essentially of a volatile cyclosiloxane ranging from about 10% to about 90% by weight of said composition and a translucent mixture of an oil or glyceride ester and a particulate carbohydrate, said mixture ranging from about 10% to about 90% by weight of said composition, said oil or glyceride ester ranging from about 5:1 to about 1:10 by weight of said particulate carbohydrate in said mixture, said composition optionally comprising at least one additive selected from the group consisting of active agents, fragrances, coloring additive, emollients, surfactants, medicinal and fill formers.

2. The composition according to claim 1 wherein said oil or glyceride ester ranges from about 5:1 to about 1:3 by weight of said particulate carbohydrate in said mixture.

3. The composition according to claim 1 wherein said oil or glyceride ester ranges from about 2:1 to about 1:2 by weight of said particulate carbohydrate in said mixture.

4. The composition according to claim 1 wherein said particulate carbohydrate is selected from the group consisting of amylopectin, amylose, dextrin, glycogen, polysaccarides derived from algae, starch, cellulose, cellulose ethers and mixtures, thereof.

5. The composition according to claim 1 wherein said particulate carbohydrate is starch.

6. The composition according to claim 5 wherein said starch is selected from the group consisting of corn starch, wheat starch, rice starch, tapioca starch and potato starch.

7. The composition according to claim 1 wherein said particulate carbohydrate is milled to a particle size of about 10 microns or less.

8. The composition according to claim 5 wherein said particulate carbohydrate is milled to a particle size of about 10 microns or less.

9. The composition according to claim 5 wherein said starch is a pharmaceutical or food grade.

10. The composition according to claim 1 wherein said volatile cyclosiloxane is selected from the group consisting of decamethylcyclopentasiloxane, octamethylcyclotetrasiloxane, dodecamethylcyclohexasiloxane and mixtures thereof.

11. The composition according to claim 10 wherein said oil is selected from the group consisting of petrolatum, mineral oil and mixtures, thereof.

12. The composition according to claim 1 wherein said glyceride ester is a mono-, di- or tri-glyceride obtained by the reaction of glycerol and at least one fatty acid selected from the group consisting of oleic acid, linoleic acid and linolenic acid.

13. The composition according to claim 1 wherein said medicinals are selected from the group consisting of camphor, menthol, zinc oxide, sulfur and a vitamin.

14. An antiperspirant composition consisting essentially of a volatile cyclosiloxane ranging from about 10% to about 70% by weight of said composition; a translucent mixture of an oil or glyceride ester and a particulate carbohydrate, said translucent mixture ranging from about 15% to about 70% by weight of said composition, said oil or glyceride ester ranging from about 5:1 to about 1:3 by weight of said particulate carbohydrate in said mixture; and about 5% to about 35% by weight of an antiperspirant material.

15. The composition according to claim 14 wherein said oil or glyceride ester ranges from about 5:1 to about 1:2 by weight of said particulate carbohydrate in said mixture.

16. The composition according to claim 14 wherein said oil or glyceride ester ranges from about 2:1 to about 1:1 by weight of said particulate carbohydrate.

17. The composition according to claim 15 wherein said volatile cyclosiloxane ranges from about 15% to about 50% by weight of said composition, said mixture ranges from about 20% to about 55% by weight of said composition and said antiperspirant material ranges from about 20% to about 30% by weight of said composition.

18. The composition according to claim 15 wherein said volatile cyclosiloxane ranges from about 35% to about 70% by weight of said composition, said mixture ranges from about 15% to about 40% by weight of said composition and said antiperspirant material ranges from about 20% to about 30% by weight of said composition.

19. The composition according to claim 15 wherein said particulate carbohydrate is starch.

20. The composition according to claim 15 wherein said starch is selected from the group consisting of corn starch, wheat starch, rice starch, tapioca starch and potato starch.

21. The composition according to claim 19 wherein said particulate carbohydrate is milled to a particle size of about 10 microns or less.

22. The composition according to claim 15 wherein said particulate carbohydrate is milled to a particle size of about 10 microns or less.

23. The composition according to claim 15 wherein said antiperspirant material is selected from the group consisting of inorganic and organic salts of aluminum, zirconium and zinc and mixtures thereof, aluminum halides, aluminum hydroxy halides, zirconyloxide halides, aluminum chlorhydroxide salts, zirconyl hydroxychlorides, zirconium salt complexes containing aluminum and glycine, oil of witch hazel, tea tree oil and mixtures, thereof.

24. The composition according to claim 15 wherein said volatile cyclosiloxane is selected from the group consisting of decamethylcyclopentasiloxane, octamethylcyclotetrasiloxane, dodecamethylcyclohexasiloxane and mixtures thereof.

25. The composition according to claim 15 wherein said oil is selected from the group consisting of petrolatum, mineral oil and mixtures, thereof.

26. The composition according to claim 15 wherein said glyceride ester is a mono-, di- or tri-glyceride obtained by the reaction of glycerol and at least one fatty acid selected from the group consisting of oleic acid, linoleic acid and linolenic acid.

27. A cosmetic or pharmaceutical composition consisting essentially of a volatile cyclosiloxane ranging from about 10% to about 90% by weight of said composition; a translucent mixture glyceride ester and a particulate carbohydrate, said mixture ranging from about 9.999% to about 89.999% by weight of said composition, said or glyceride ester ranging from about 5:1 to about 1:3 by weight of said particulate carbohydrate in said mixture; and about 0.001% to about 40% by weight of an active agent selected from the group consisting of anti-fungal agents, antimicrobial agents, anti-inflammatory agents, anti-puritic agents, anti-acne agents, hemostatic agents, anti-histaminic agents, medicinals and mixtures, thereof.

28. The composition according to claim 27 wherein said oil or glyceride ester ranges from about 5:1 to about 1:2 by weight of said particulate carbohydrate.

29. The composition according to claim 27 wherein said oil or glyceride ester ranges from about 2:1 to about 1:2 by weight of said particulate carbohydrate.

30. The composition according to claim 27 wherein said particulate carbohydrate is selected from the group consisting of amylopectin, amylose, dextrin, glycogen, polysaccarides derived from algae, starch, cellulose, cellulose ethers and mixtures, thereof.

31. The composition according to claim 27 wherein said particulate carbohydrate is starch.

32. The composition according to claim 31 wherein said starch is selected from the group consisting of corn starch, wheat starch, rice starch, tapioca starch and potato starch.

33. The composition according to claim 27 wherein said particulate carbohydrate is milled to a particle size of about 10 microns or less.

34. The composition according to claim 31 wherein said starch is milled to a particle size of about 10 microns or less.

35. The composition according to claim 31 wherein said starch is of pharmaceutical or food grade.

36. The composition according to claim 27 wherein said volatile cyclosiloxane is selected from the group consisting of decamethylcyclopentasiloxane, octamethylcyclotetrasiloxane, dodecamethylcyclohexasiloxane and mixtures thereof.

37. The composition according to claim 27 wherein said oil is selected from the group consisting of petrolatum, mineral oil and mixtures, thereof.

38. The composition according to claim 27 wherein said glyceride ester is a mono-, di- or tri-glyceride obtained by the reaction of glycerol and at least one fatty acid selected from the group consisting of oleic acid, linoleic acid and linolenic acid.

39. The composition according to claim 27 wherein said medicinals are selected from the group consisting of zinc oxide, sulfur, menthol, camphor, vitamin A, vitamin D, vitamin E and mixtures thereof.

40. The composition according to claim 34 wherein said active agent is selected from the group consisting of anti-fungal agents, anti-acne agents, antimicrobial agents, anti-inflammatory agents, and mixtures thereof.

41. A non-aqueous, volatile cyclosiloxane-free translucent cosmetic or pharmaceutical film-forming composition consisting essentially of:

at least about 60% by weight of a translucent mixture comprising an oil or glyceride ester and a particulate carbohydrate in a weight ratio ranging from about 5:1 to about 1:3; where in said oil or glyceride ester being included at about 20% to about 85% by weight of said composition and said particulate carbohydrate being included in said composition at about 10% to about 70% by weight and about 0.001% to about 40% by weight of at least one additive selected from the group consisting of anti-fungal agents, antiperspirant materials, antimicrobial agents, anti-inflammatory agents, anti-puritic agents, anti-acne agents, hemostatic agents, anti-histaminic agents, medicinals, fragrances, coloring additives, emollients, surfactants, film formers and mixtures thereof.

42. The composition according to claim 41 wherein said medicinals are selected from the group consisting of camphor, menthol, zinc oxide, sulfur and a vitamin.

* * * * *